United States Patent
Krosney et al.

(10) Patent No.: US 9,480,768 B2
(45) Date of Patent: Nov. 1, 2016

(54) AIR STERILIZATION AND DISINFECTION METHOD

(71) Applicants: Mark D. Krosney, Port St. Lucie, FL (US); William E. Reisenauer, Commack, NY (US)

(72) Inventors: Mark D. Krosney, Port St. Lucie, FL (US); William E. Reisenauer, Commack, NY (US)

(73) Assignee: CLEANCO BIOSCIENCE GROUP, LLC, Port Saint Lucie, FL (US)

( * ) Notice: Subject to any disclaimer, the term of this patent is extended or adjusted under 35 U.S.C. 154(b) by 0 days.

(21) Appl. No.: 14/527,449

(22) Filed: Oct. 29, 2014

(65) Prior Publication Data

US 2015/0078960 A1 Mar. 19, 2015

Related U.S. Application Data

(62) Division of application No. 13/951,598, filed on Jul. 26, 2013, now Pat. No. 8,900,519.

(60) Provisional application No. 61/676,407, filed on Jul. 27, 2012.

(51) Int. Cl.
  *A62B 7/08* (2006.01)
  *A61L 9/20* (2006.01)
  *B01D 53/00* (2006.01)

(52) U.S. Cl.
  CPC ............... *A61L 9/20* (2013.01); *B01D 53/007* (2013.01); *A61L 2209/14* (2013.01); *A61L 2209/16* (2013.01); *B01D 2257/91* (2013.01); *B01D 2259/804* (2013.01)

(58) Field of Classification Search
  CPC ..... A61L 9/20; A61L 2209/14; B01J 19/123
  USPC .................................................. 422/120, 121
  See application file for complete search history.

(56) References Cited

U.S. PATENT DOCUMENTS

| | | | |
|---|---|---|---|
| 5,505,904 | A | 4/1996 | Haidinger et al. |
| 6,053,968 | A | 4/2000 | Miller |
| 6,797,044 | B2 | 9/2004 | Ou Yang et al. |
| 7,175,814 | B2 | 2/2007 | Dionisio |
| 7,498,004 | B2 | 3/2009 | Saccomanno |
| 2005/0242013 | A1 | 11/2005 | Hunter et al. |
| 2006/0159594 | A1* | 7/2006 | Parker ...................... A61L 9/20 422/121 |
| 2007/0196235 | A1 | 8/2007 | Shur et al. |
| 2009/0084734 | A1 | 4/2009 | Yencho |

(Continued)

*Primary Examiner* — Kevin Joyner
(74) *Attorney, Agent, or Firm* — The Marbury Law Group, PLLC

(57) ABSTRACT

An apparatus (100 and/or 200) and corresponding method (500) for air sterilization and disinfection can include an electronics and control module (110 and/or 210), a means for drawing air from the surrounding environment into the apparatus (120 and/or 220), an air management chamber (130 and/or 230), and a housing (170 and/or 270). The means for drawing air from the surrounding environment into the apparatus (120 and/or 220) mobilizes latent pathogens in the environment and draws them into the apparatus (100 and/or 200) for sterilization and disinfection. The air management chamber (130 and/or 230) provides for exposure of the airborne pathogens to UV radiation, via UV LEDs (150 and/or 250), with a dosage sufficient to penetrate the cell walls and destroy the pathogens. The electronics and control module (110 and/or 210) powers the apparatus (100 and/or 200) and interfaces with the electronic components. The housing (170) forms the outer shell of the apparatus (100).

12 Claims, 5 Drawing Sheets

(56) References Cited

U.S. PATENT DOCUMENTS

| | | |
|---|---|---|
| 2010/0132715 A1 | 6/2010 | Litz |
| 2010/0260644 A1 | 10/2010 | Day et al. |
| 2011/0033346 A1 | 2/2011 | Bohlen et al. |
| 2012/0273340 A1* | 11/2012 | Felix .................. B01D 53/007 204/157.3 |
| 2013/0313104 A1 | 11/2013 | Yates |
| 2014/0030144 A1 | 1/2014 | Krosney |

* cited by examiner

```
500
```

- 502 — draw ambient air through a preliminary particulate filter into an air management chamber with enough convective air exchange to mobilize latent pathogens
- 504 — direct the air flow into one or a plurality of reaction tubes within the air management chamber
- 506 — expose the air flow to UV radiation
- 508 — reflect the UV radiation within the reaction tubes
- 510 — Increase the exposure time of the air to the UV radiation by creating a turbulent flow
- 512 — expose the air flow to UV radiation, at a wavelength known to traverse the cellular walls, for greater than one second
- 514 — monitor the UV levels in the air management chamber
- 516 — determine if the irradiance level in the air management chamber is adequate for the desired pathogen kill rate
- 518 — indicate to the user that the apparatus is or is not working
- 520 — expose the air flow to copper or copper alloy surfaces
- 522 — direct the airflow through a HEPA filter
- 524 — direct the airflow through a silver ion plus citric acid infused material
- 526 — expel clean, sanitized air back into the surrounding environment

FIG. 5

AIR STERILIZATION AND DISINFECTION METHOD

CROSS-REFERENCE TO RELATED APPLICATIONS

This application is a continuation of U.S. patent application Ser. No. 13/951,598, now U.S. Pat. No. 8,900,519 filed on Jul. 26, 2013, which claims the benefit of U.S. Provisional Patent Application No. 61/676,407, filed on Jul. 27, 2012, which are all incorporated herein by reference.

STATEMENT REGARDING FEDERALLY SPONSORED RESEARCH OR DEVELOPMENT

Not applicable.

FIELD OF THE INVENTION

This invention relates generally to air sterilization and disinfection, and more particularly to an apparatus and a method for sterilizing and disinfecting air in a hospital or hospital-like environment.

BACKGROUND OF THE INVENTION

There is a growing demand for improvements in hospital settings to reduce the transmission of pathogens. This demand is driven by hospitals that have to deal with an increasing amount of cases of infections, not caused by the patient's diagnosis upon admission, but rather, due to airborne pathogens that exist in a hospital environment. These airborne pathogens pose additional health risks to patients and result in additional costs to the hospital. There are currently two approaches to reducing in-hospital transmitted contamination. The first involves decontamination of hospital room surfaces between occupancies. This can be accomplished by irradiating the room and all of its surfaces with high-level ultraviolet (UV) radiation or by spraying the room with hydrogen peroxide mist. The room must be unoccupied and isolated and if anyone wishes to enter the room during this process, significant protective equipment must be worn. Secondly, treatment of room air is an issue. A variety of units utilizing UV or HEPA type filtering or a combination of the two are currently available. There are also UV units with powerful fans that can be used to create positive or negative pressurized areas. For the area being treated, some installation of UV lighting inside ventilation ducting is also used.

Devices produced with traditional technologies have been large, difficult to locate optimally, and their performance degrades substantially with time. Currently available compact systems do not provide adequate airflow and/or pathogen kill rate. Conversely, more effective devices are currently large and difficult to maintain. Conventional UV-based systems use fluorescent tube elements. To produce adequate intensity, several tubes are often grouped together. The geometry of the tubes and their limited output per tube produces a bulky and cumbersome apparatus. The UV output of the tubes decays with time due to deterioration and with external factors such as dust settling on the tubes. Maintenance and replacement of the UV tubes is a laborious process. The size required by these units consumes critical space, which is crucial in a hospital environment. Because of their size, they cannot be located in the optimum locations to maximize their benefit. Typical units have three to four square foot cross sections and can be six feet in length and weigh about 100 pounds.

It would be desirable to have an apparatus that reduces or removes airborne pathogens, which can be used while the room is still occupied. Furthermore, it would also be desirable to have an apparatus that is portable and unobtrusive while producing a sufficiently high flow rate to be effective. Still further, it would be desirable to have an apparatus whose performance does not significantly degrade over time and is easy to maintain. Therefore, there currently exists a need in the industry for an apparatus and associated method that is compact, portable, and highly effective in reducing or removing airborne pathogens.

Currently there are a number of solutions for air purification in a hospital (or hospital-like) environment. Some of these solutions attempt to purify air by utilizing UV fluorescent tubes, but these solutions fail to meet the needs of the industry because they are large, cumbersome, and difficult to maintain. Unlike existing UV disinfection devices available on the market today, the present invention uses UV Light-Emitting Diodes (LEDs) as opposed to fluorescent tubes. LEDs are solid state devices that enjoy many advantages over fluorescent tubes. LEDs are more robust and perform better under adverse environmental conditions such as shock and vibration. LEDs do not require high voltage, so they are safer to troubleshoot and repair. They do not suffer glass breakage and their disposal does not constitute hazardous waste.

Other solutions attempt to utilize UV LEDs, but these solutions are similarly unable to meet the needs of the industry because they are unable to modulate the airflow in such a way as to provide the necessary UV radiation dosage to adequately kill the pathogens. Unlike existing solutions attempting to utilize UV LEDs, the present invention combines the irradiance field created by the UV LEDs with a modulated airflow in order to provide the necessary UV dosage to adequately kill the airborne pathogens.

The UV spectrum is divided into portions by wavelength. UVB and UVC radiation represents that portion of the spectrum that is capable of damaging biological organisms. High energy UVC photons are those with wavelengths shorter than 290 nm and are capable of traversing cellular walls. UVC radiation is used as a germicidal in order to kill airborne pathogens. UVB radiation is characterized by wavelengths between 290 and 320 nm and is also damaging to biological organisms. In order to kill pathogens, the UV radiation needs to be of a wavelength that can traverse the cellular walls. Studies have shown that the effective wavelengths for killing pathogens, such as bacteria, are in the 200 to 320 nm range. Still other studies indicate that wavelengths between 240 and 280 nm are most effective in killing a broad range of pathogens, with peak effectivity around 260 to 270 nm. The intensity or "flux" of the UV radiation is an important consideration in evaluating the effects of the UV radiation at the pathogenic level. The "UV radiation flux density" is related to the amount of radiation at the specified wavelength that reaches the surface of the pathogens. This UV radiation flux is also referred to as the "UV irradiance". In the interaction of radiant energy with biological organisms, both wavelength and irradiance, or radiation flux, must be considered. The "UV dosage" required to effectively kill airborne pathogens is derived from a combination of UV wavelength, radiation flux, and time of exposure. The "dwell" or "residence" time is defined as the amount of time that the airborne pathogens remain exposed to the UV radiation field and are irradiated by the UV LEDs. The desired pathogen kill rate can then be optimized by properly balancing the UV LED wavelength, radiation flux, and dwell time.

Information relevant to attempts to address the problems found in the current state of the art, as described above, can be found in U.S. Pat. Nos. 6,797,044, 7,175,814, 6,053,968, 6,939,397, and 5,505,904, as well as U.S. Patent Application Nos. 20110033346, 201000132715, 20070196235, 20100260644, and 20050242013. However, each one of these references suffers from one or more of the following disadvantages: it is large or bulky; it uses fluorescent tubes; it employs a low dwell time; it achieves a low air flow rate; it does not adequately balance UV wavelength, radiation flux, and dwell time for an effective pathogen kill rate.

The present invention is unique when compared with other known devices and methods because the present invention provides: (1) a compact footprint; (2) effective pathogen removal; and (3) ease of maintenance.

The present invention is unique in that it is structurally different from other known devices or solutions. More specifically, the present invention is unique due to the presence of: (1) an air management chamber comprising a single or a plurality of reaction tubes; (2) UV LEDs embedded in the walls of the reaction tubes; and (3) specified areas of turbulent flow within the reaction tubes that increase the exposure to the UV radiation without sacrificing the air flow rate through the air management chamber.

SUMMARY OF THE INVENTION

The present invention relates to an apparatus and a method associated with the apparatus. With respect to the apparatus, it is a compact, highly effective air sterilization and disinfection apparatus, which delivers clean, pure air right where it is needed. The apparatus combines wavelength-specific, high-output UV LEDs with an airflow management chamber that facilitates the necessary UV dosage by increasing the dwell time of the airflow being treated. This apparatus can be used in hospitals, clinics, operating rooms, and other environments where it is desired to reduce or eliminate airborne pathogens. The compact, quiet, and unobtrusive nature of this apparatus makes it particularly well suited for use in hospital environments.

Generally, the apparatus comprises an electronics and control module, a means of drawing room air into the apparatus, an air management chamber with one or more reaction tubes, an array of wavelength-specific, high-output UV LEDs, and a housing, which, generally speaking, are configured as follows: the electronics and control module is connected to, but preferably not in the path of the air flow; a means of drawing room air into the apparatus is located at the apparatus inlet and forces air into the inlet of the air management chamber and one or more reaction tubes; an array of UV LEDs is located within the air management chamber, coupled to the reaction tubes in a manner that maximizes contact with the airflow; and a housing covers the entire apparatus.

With respect to the apparatus it should be further noted that the selection of the wavelength of the UV LEDs as well as the design of the air management chamber and reaction tubes is critical in order to manage the level and duration of UV light dosage in order to effectively sanitize the room air without compromising the desired airflow rate.

Generally, the steps to carry out the method associated with the apparatus are comprised of:

Drawing room air into the airflow management chamber at a rate of between 180 to 300 cu. Ft./min;

Exposing the air to UV radiation at a wavelength known to traverse the cellular walls;

Creating a turbulent flow within the air management chamber such that airborne pathogens are exposed to the UV radiation for a specified amount of time in order to achieve the desired kill rate; and Expelling the sanitized air back into the surrounding environment.

In an embodiment of the present invention, an air sterilization and disinfection apparatus can include the following components: an electronics and control module; a fan; an air management chamber with an inlet and an outlet; UV LEDs; and a housing. The electronics and control module regulates the electrical power input into the apparatus and drives the fan and UV LEDs. The electronics and control module shall operate with conventionally available power supplies and contain a circuit breaker. The fan shall be selected such as to provide the desired airflow rate. The fan shall be quiet and compact and have a dust particulate filter at the input. The fan module shall provide enough convective air exchange to mobilize latent pathogens and thereby promote effective cleaning. A flow rate within the range of 180 to 300 cu Ft/min will provide effective cleaning of a typical hospital room. The air management chamber is the key component in the design of the apparatus. The air management chamber is comprised of one or more reaction tubes. Each reaction tube is designed to sustain a specific volumetric throughput. The reaction tube further locates the UV LEDs in order to achieve the desired UV radiation flux density throughout the flow area. The UV LEDs are affixed to the reaction tube such that they do not impede the airflow required yet permit any necessary wiring and cooling. The reaction tube is further designed such as to modulate the airflow within the tube in order to achieve the desired dwell time by creating a turbulent flow, characterized as a flow having a Reynolds Number above approximately 4000. The dwell time is defined as the amount of time that the airborne pathogens remain exposed to the UV radiation field and are irradiated by the UV LEDs. A dwell time of greater than one second is desired. The reaction tube and air management chamber are designed such as to prevent the escape of any UV radiation. The materials for the reaction tube are chosen such as to maximize the UV reflectivity of the internal surfaces in order to maintain the highest possible radiant flux. UV LEDs are chosen for this apparatus because of their size, power, and long life. The UV LEDs are selected based upon the desired wavelength and power rating. The number and distribution of these UV LEDs in the reaction tubes are to be such as to maximize the radiant flux within each tube. The housing protects the user from exposure to the internal components as well as any UV radiation and has an inlet opening coupled to the airflow input to the air management chamber and an outlet opening coupled to the airflow output from the air management chamber.

These components are mechanically connected and arranged such that the fan is located at the inlet of the air management chamber, the UV LEDs are located within the air management chamber, and the electronics and control module is located outside of the air flow path. The housing encases the individual components.

The method associated with this embodiment of the apparatus is comprised of the following steps:

Creating enough convective air exchange to mobilize latent pathogens and thereby promote effective cleaning;

Forcing the air with the pathogens into the air management chamber;

Exposing the air with the pathogens in the air management chamber to UV radiation with a dosage such that the UV wavelength can traverse the cellular walls of the pathogens and with a dwell time sufficient to achieve the desired pathogen kill rate; and Expelling the sanitized air back into the surrounding environment.

In another embodiment of the present invention, an air sterilization and disinfection apparatus may also have one or more of the following: a UV detector to monitor the irradiance levels in the air management chamber; a light, display, or other visual indicator to indicate to the user that the apparatus is working; a supplemental filter at the outlet of the air management chamber; a supplemental filter that is a HEPA filter; a supplemental filter that is a material that is treated with a silver ion and citric acid suspension or other metal ion compounds; an air management chamber with a plurality of reaction tubes; a manifold to direct the air flow from a single fan into a plurality of reaction tubes; an array of fans where a single fan directs air flow into a single reaction tube; a reaction tube where the turbulent flow is created using a single or multiple reverse steps, or areas of sudden expansion, where the tube diameter increases abruptly from one section of the airflow to the next; a reaction tube where the turbulent flow is created using a single or a plurality of v-gutters; a single or a plurality of copper or copper alloy structures within a reaction tube in order to have the airflow come into contact with the copper or copper alloy, which are naturally antimicrobial; a reaction tube where the dwell time is increased by means of a circular or spiral airflow path; a UV LED array that is mounted on rigid circuit boards; a UV LED array that is mounted on flexible circuit boards; a plurality of UV LEDs mounted in a staggered pattern in the reaction tube in order to optimize the radiant flux density within the reaction tube; an array of UV LEDs of different wavelengths in order to kill different pathogens that may not share the same cell wall UV transmissivity characteristics.

Similarly, the method associated with this embodiment of the present invention may also comprise one or more of the following steps:

Removing additional pathogens by passing the air through a HEPA filter; or also

Removing additional pathogens by passing the air through a material that has been treated with a silver ion and citric acid suspension; or also Exposing the airflow within the air management chamber to copper or copper alloy structures; or also Monitoring the irradiance levels in the air management chamber; or also Providing a visual indication to the user that the apparatus is working.

In yet another embodiment of the present invention, an air sterilization and disinfection apparatus is comprised of the following components: an electronics and control module; a plurality of fans; an air management chamber with a plurality of reaction tubes; said reaction tubes having a plurality of areas of sudden expansion, thereby creating a turbulent flow along the interior walls of the reaction tube, said turbulent flow characterized by a Reynolds Number above approximately 4000 and a dwell time of greater than one second; said reaction tubes also having an array of UV LEDs mounted within the tube walls such as to maximize the radiant flux within the tube without obstructing the air flow; said array comprising UV LEDs of wavelengths less than 320 nm; a UV sensor mounted in each reaction tube in order to monitor the irradiance level in each tube; an externally visible indicator to tell the user that the apparatus is working; a plurality of v-gutters; a plurality of copper or copper alloy structures; a HEPA filter; a silver ion and citric acid infused filter material; and an external housing.

These components are related as follows: the electronics and control module is mounted to the housing outside of the airflow path; the fans are electrically connected to the electronics and control module and force air into the air management chamber; the air management chamber is comprised of reaction tubes, that are coupled to the fans in order to receive the airflow without loss or leaks; the UV LED arrays are electrically connected to the electronics and control module and are fixedly attached to mated openings in the walls of the reaction tube such that the UV LED array circuit boards are outside of the reaction tube and the UV LEDs irradiate inside the reaction tube; the UV detector is electrically connected to the electronics and control module and fixedly attached to a mated opening in the wall of the reaction tube such that the detector can monitor irradiance levels inside of the reaction tube; the v-gutters are mechanically attached inside the reaction tube; the supplemental HEPA and silver ion plus citric acid filters are located at the outlet of the air management chamber air flow path; and the housing encloses the entire apparatus. It should further be noted that: the reaction tubes can be made out of various materials, however, polished aluminum is lightweight, inexpensive, and is UV reflective thereby promoting adequate UV flux density within the reaction tube; the v-gutters may be made of polished aluminum, copper, or copper alloy; the reaction tubes and UV LED arrays are assembled such that the UV radiation is contained completely within the reaction tube; and the supplemental filters are mounted such as to be easily replaceable by the user.

The method associated with an embodiment of the apparatus is comprised of the following steps:

Drawing ambient air through a preliminary particulate filter into an air management chamber with enough convective air exchange to mobilize latent pathogens;

Directing the air flow into a plurality of reaction tubes within the air management chamber;

Exposing the air flow to UV radiation;

Reflecting the UV radiation within the reaction tubes;

Increasing the exposure time of the air to the UV radiation by creating a turbulent flow characterized by a Reynolds Number above approximately 4000;

Exposing the air flow to UV radiation for greater than one second;

Monitoring the UV levels in the air management chamber;

Determining if the irradiance level in the air management chamber is adequate for the desired pathogen kill rate;

Indicating to the user that the apparatus is or is not working;

Exposing the air flow to copper or copper alloy surfaces;

Directing the airflow through a HEPA filter;

Directing the airflow through a silver ion plus citric acid infused material; and Expelling clean, sanitized air back into the surrounding environment.

BRIEF DESCRIPTION OF THE DRAWINGS

These and other features, aspects, and advantages of the present invention will become better understood with regard to the following description, appended claims, and accompanying drawings where:

FIG. 1 shows a perspective view of an air sterilization and disinfection device in accordance with an embodiment of the present invention;

FIG. 5 shows a flow chart illustrating a method for air sterilization and disinfection device in accordance with an embodiment of the present invention.

DETAILED DESCRIPTION OF THE DRAWINGS

Figure 1:
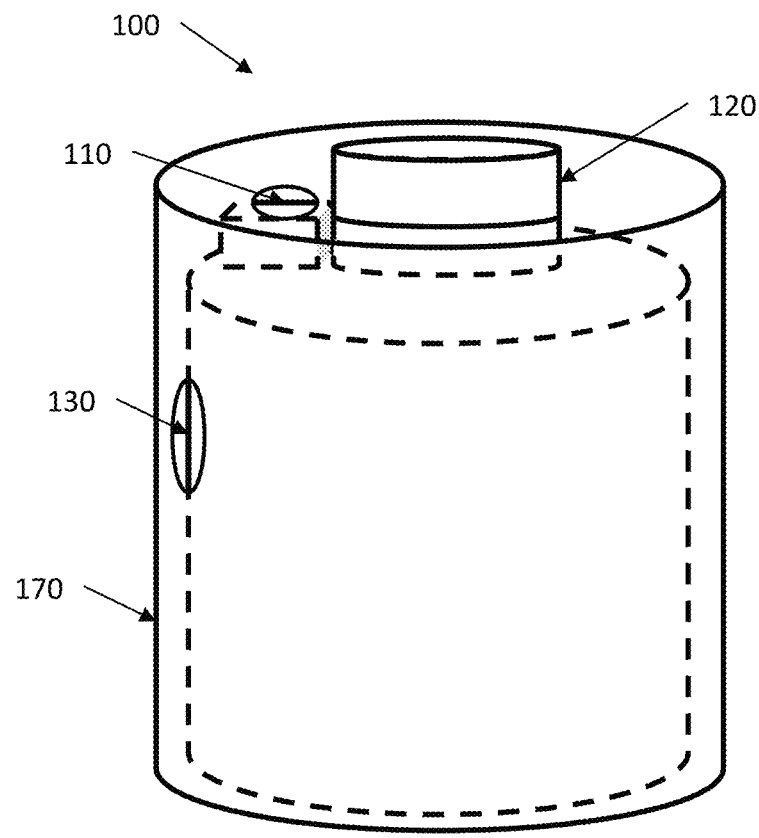

In the Summary of the Invention above and in the Detailed Description of the Drawings, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm.

While the specification concludes with claims defining the features of embodiments of the invention that are regarded as novel, it is believed that the invention will be better understood from a consideration of the following description in conjunction with the figures, in which like reference numerals are carried forward.

One embodiment, in the form of an air sterilization and disinfection apparatus 100 as shown in FIGS. 1-4, can comprise: an electronics and control module 110; a fan 120; an air management chamber 130; and a housing 170.

Figure 2:
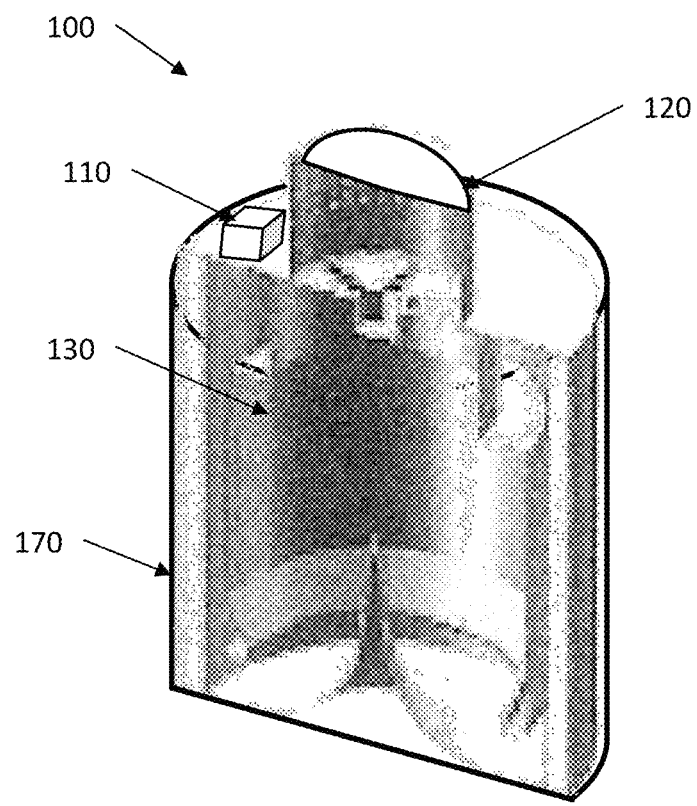
FIG. 2 shows a sectional perspective view of the device of FIG. 1 in accordance with an embodiment of the present invention.
Figure 3:
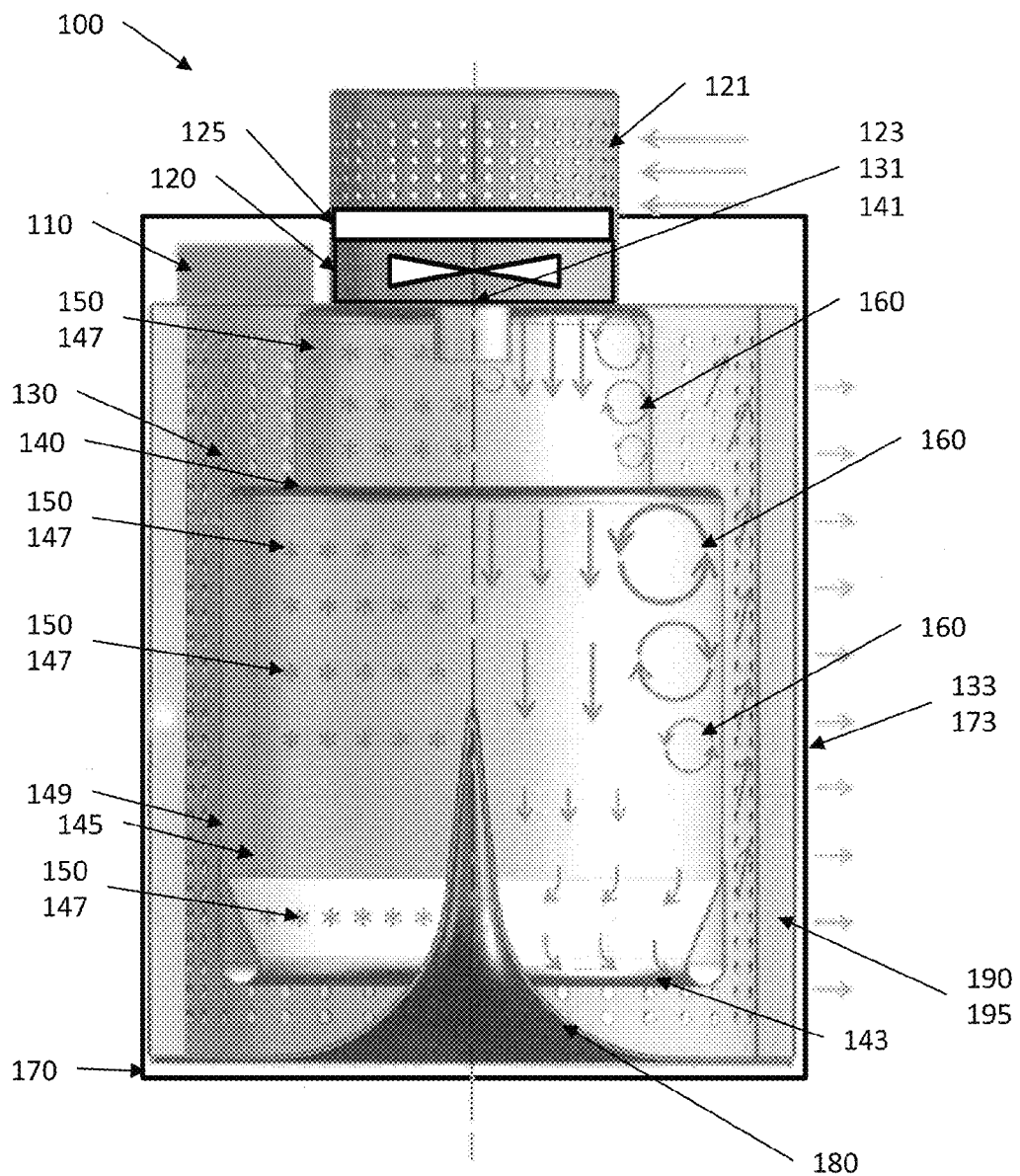
FIG. 3 shows a front sectional view of the device of FIG. 1 in accordance with an embodiment of the present invention.

Referring to FIGS. 1, 2, and 3, in this embodiment the electronics and control module 110 regulates the electrical power input into the apparatus 100. The electronics and control module 110 operates with conventionally available power sources and comprises a circuit breaker means, a processor means, and a voltage regulator means. The electronics and control module 110 is located generally within the housing 170 but outside the path of the airflow through the air management chamber 130. The electronics and control module 110 may also optionally be located outside of the housing 170, or in its own housing, and be electrically coupled with the apparatus. The fan 120 shall be selected such as to provide an airflow rate within the range of 180 to 300 cu Ft/min. The fan 120 is electrically coupled to the electronics and control module 110.

Referring to FIG. 3, the fan 120 shall be quiet and compact and have a dust particulate filter means 125 at the fan input 121. The fan output 123 is coupled to the air management chamber input 131 using an airtight sealing means such as to prevent air leaks. The air management chamber 130 is comprised of one or more reaction tubes 140. Each reaction tube 140 has an inlet 141 coupled to the inlet 131 of the air management chamber 130 using an airtight sealing means, and an outlet 143 coupled to the outlet 133 of the air management chamber 130. The reaction tube 140 further locates the UV LEDs 150 in order to achieve the desired UV radiation flux density throughout the area of turbulent flow 160. The UV LEDs 150 are affixed to the reaction tube 140 via mated openings 147 distributed along the wall of the reaction tube 140, the mated openings 147 traversing from the external surface 149 to the internal surface 145 of the reaction tube 140, such that the UV LEDs 150 do not impede the airflow required yet permit any necessary wiring and cooling. The reaction tube 140 is further designed such as to modulate the airflow within the tube in order to achieve the desired dwell time by creating an area of turbulent flow 160. The reaction tubes 140 and air management chamber 130 comprise such sealing means as to prevent the escape of any UV radiation. The materials for the reaction tube 140 are chosen such as to maximize the UV reflectivity of the internal surfaces 145 in order to maintain the highest possible radiant flux. An embodiment of the apparatus may include a reaction tube 140 where the internal surface 145 is aluminum, or a material having >95% reflectance. The reaction tubes 140 may also comprise one or a plurality of v-gutters 180 located in the path of the airflow and fixedly attached to the reaction tube 140. The v-gutters 180 may be made of a UV reflective material such as polished aluminum, or a naturally germicidal material such as copper or copper alloy.

An embodiment of an air sterilization and disinfection apparatus as shown in FIGS. 1, 2, and 3, may also comprise a HEPA filter 190 located in the path of the airflow coupled to the outlet 143 of the reaction tube 140.

An embodiment of an air sterilization and disinfection apparatus as shown in FIGS. 1, 2, and 3, may also comprise a silver ion plus citric acid infused filter 190 located in the path of the airflow coupled to the outlet 143 of the reaction tube 140.

An embodiment of an air sterilization and disinfection apparatus as shown in FIGS. 1, 2, and 3, may also comprise a housing 170 that protects the user from exposure to the UV radiation and has an inlet opening 171 coupled to the air management chamber input 131 and outlet opening 173 coupled to the air management chamber outlet 133.

Figure 4:
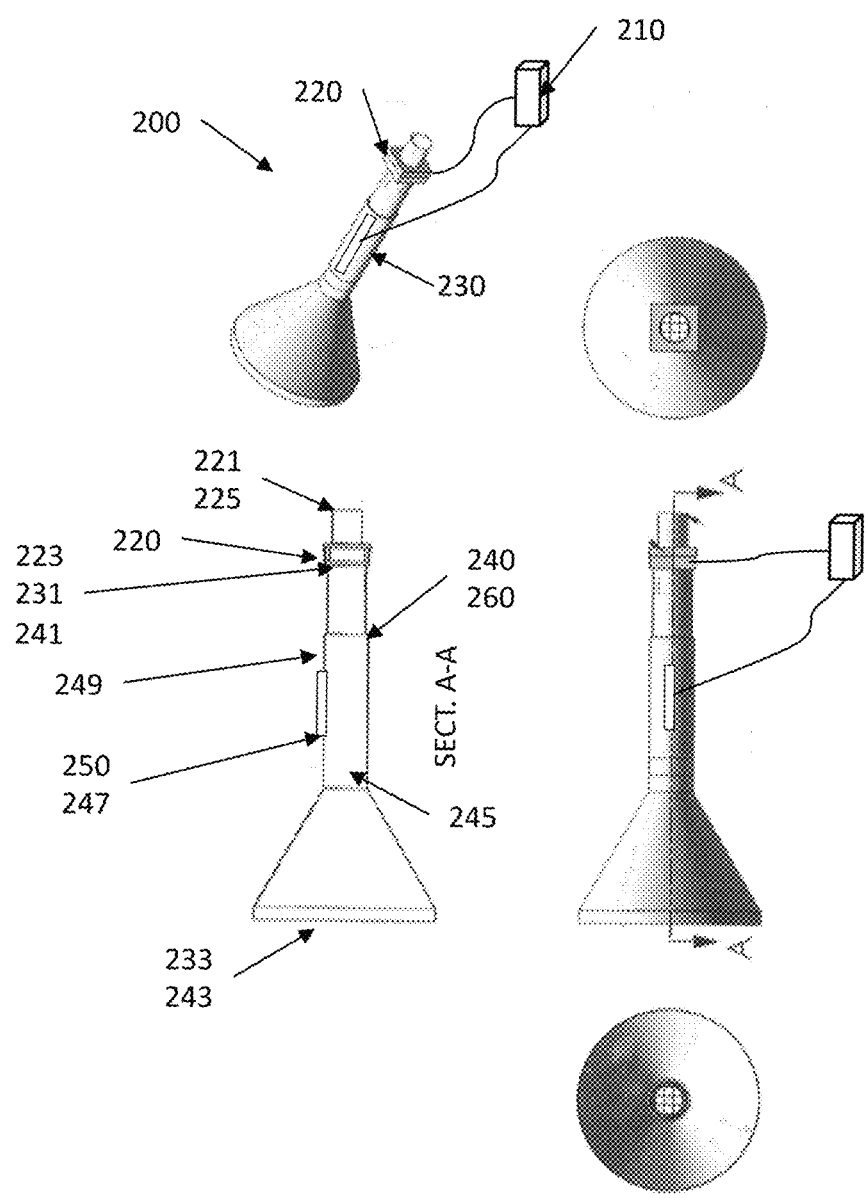
FIG. 4 shows multiple views of an air sterilization and disinfection device in accordance with an embodiment of the present invention.

Referring to FIG. 4, in this embodiment, an air sterilization and disinfection apparatus 200 comprises an electronics and control module 210, a fan 220, and an air management chamber 230. In this embodiment the electronics and control module 210 regulates the electrical power input into the apparatus 200. The electronics and control module 210 operates with conventionally available power sources and comprises a circuit breaker means, a processor means, and a voltage regulator means. The electronics and control module 220 is located outside of the airflow path through the air management chamber 230. The electronics and control module 210 is electrically coupled to the fan 220 and the UV LEDs 250. The fan 220 shall be selected such as to provide an airflow rate within the range of 180 to 300 cu Ft/min. The fan 220 is electrically coupled to the electronics and control module 210. The fan 220 shall be quiet and compact and have a dust particulate filter means 225 at the fan input 221. The fan output 223 is coupled to the air management chamber input 231 using an airtight sealing means such as to prevent air leaks. The air management chamber 230 is comprised of a reaction tube 240 with an area of turbulent flow 260 and an array of UV LEDs 250. The reaction tube 240 has an inlet 241 coupled to the inlet 231 of the air management chamber 230 using an airtight sealing means, and an outlet 243 coupled to the outlet 233 of the air management chamber 230. The reaction tube 240 further locates the UV LEDs 250 in order to achieve the desired UV radiation flux density throughout the area of turbulent flow 260. The UV LEDs 250 are affixed to the reaction tube 240 via mated openings 247 distributed along the wall of the reaction tube 240, the mated openings 247 traversing from the external surface 249 to the internal surface 245 of the reaction tube 240, such that the UV LEDs 250 do not impede the airflow required yet permit any necessary wiring and cooling. The reaction tube 240 is further designed such as to modulate the airflow within the tube in order to achieve the desired dwell time by creating an area of turbulent flow 260. The reaction tube 240 and air management chamber 230 comprise such sealing means as to prevent the escape of any UV radiation. The materials for the reaction tube 240 are chosen such as to maximize the UV reflectivity of the internal surfaces 245 in order to maintain the highest possible radiant flux. An embodiment of the apparatus such as that shown in FIG. 4 may include a reaction tube 240 where the internal surface 245 is aluminum (reflectance >75%) or other high reflectance material (e.g., aluminum compound (reflectance >90%), ePTFE (reflectance >99%), etc.).

Referring to FIG. 5, a flow chart is shown illustrating a method 500 of air sterilization and disinfection for an embodiment of the present invention. The method 500 can include the step 512 of exposing airborne pathogens to UV radiation, at a wavelength known to traverse the cellular walls, for greater than one second. More specifically, the method 500 can draw ambient air through a preliminary particulate filter into an air management chamber with enough convective air exchange to mobilize latent pathogens at step 502, direct the air flow into one or a plurality of reaction tubes within the air management chamber at step 504, expose the air flow to UV radiation at step 506, reflect the UV radiation within the reaction tubes at step 508, increase the exposure time of the air to the UV radiation by creating a turbulent flow at step 510, expose the air flow to UV radiation, at a wavelength known to traverse the cellular walls, for greater than one second at step 512, monitor the UV levels in the air management chamber at step 514, determine if the irradiance level in the air management chamber is adequate for the desired pathogen kill rate at step 516, indicate to the user that the apparatus is or is not working at step 518, expose the air flow to copper or copper alloy surfaces at step 520, direct the airflow through a HEPA filter at step 522, direct the airflow through a silver ion plus citric acid infused material at step 524, and expel clean, sanitized air back into the surrounding environment in step 526.

In light of the foregoing description, it should be recognized that embodiments in accordance with the present invention can be realized in numerous configurations contemplated to be within the scope and spirit of the claims. Additionally, the description above is intended by way of example only and is not intended to limit the present invention in any way, except as set forth in the following claims.

What is claimed is:

1. A method of sterilizing and disinfecting air, the method comprising:
    creating a convective air exchange to mobilize pathogens in a room;
    forcing room air with the pathogens into an airflow management chamber, wherein the airflow management chamber comprises one or more reaction tubes;
    exposing the air with the pathogens in the air management chamber to ultraviolet (UV) radiation at a wavelength known to traverse the cellular walls;
    creating a turbulent flow within the air management chamber such that airborne pathogens are exposed to the UV radiation for a specified amount of time;
    directing the air through a HEPA filter;
    directing the air through a silver ion plus citric acid infused material; and
    expelling the sanitized and disinfected air back into the surrounding environment.

2. The method of claim 1, wherein the convective air exchange is characterized as an air flow rate of between 180 to 300 cu. Ft./min.

3. The method of claim 1, wherein the airborne pathogens are exposed to the UV radiation for greater than one second.

4. The method of claim 1, wherein the UV radiation wavelength is less than 320 nm.

5. The method of claim 1, wherein the airflow management chamber if formed from aluminum.

6. The method of claim 1, wherein the airflow management chamber is configured to prevent escape of UV radiation.

7. The method of claim 1, wherein the UV radiation is generated by at least one light emitting diode (LED).

8. A method of sterilizing and disinfecting air, the method comprising:
    drawing air through a filter into a one or more reaction tubes with a convective air exchange sufficient to mobilize latent pathogens;
    exposing the air to ultraviolet (UV) radiation within the one or more reaction tubes;
    reflecting the UV radiation within the one or more reaction tubes;
    creating a turbulent flow within the one or more reaction tubes to increase exposure time of the air to the UV radiation, wherein the air flow is exposed to UV radiation for greater than one second within the one or more reaction tubes;
    directing the air through a HEPA filter;

directing the air through a silver ion plus citric acid infused material; and expelling sterilized and disinfected air from the one or more reaction tubes.

9. The method of claim 8, further comprising:

monitoring the UV levels in the one or more reaction tubes;

determining if the irradiance level in the one or more reaction tubes is adequate for the desired pathogen kill rate; and exposing the air to antimicrobial surfaces.

10. The method of claim 8, wherein the convective air exchange is characterized as an air flow rate of between 180 to 300 cu. Ft./min.

11. The method of claim 8, wherein the UV radiation wavelength is less than 320 nm.

12. The method of claim 9, wherein the antimicrobial surfaces are chosen from the group consisting of aluminum, copper, and copper alloys.

\* \* \* \* \*